US011369625B2

(12) United States Patent
Iwaki et al.

(10) Patent No.: US 11,369,625 B2
(45) Date of Patent: Jun. 28, 2022

(54) ANTI-TUMOR AGENT, ANTI-TUMOR EFFECT ENHANCER, AND ANTI-TUMOR KIT

(71) Applicant: FUJIFILM Corporation, Tokyo (JP)

(72) Inventors: Yoshihide Iwaki, Ashigarakami-gun (JP); Tsukasa Kitahashi, Ashigarakami-gun (JP); Shinji Mima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/286,930

(22) Filed: Feb. 27, 2019

(65) Prior Publication Data

US 2019/0192546 A1 Jun. 27, 2019

Related U.S. Application Data

(63) Continuation of application No. PCT/JP2017/031074, filed on Aug. 30, 2017.

(51) Int. Cl.
| | |
|---|---|
| *A61K 31/7068* | (2006.01) |
| *A61K 47/42* | (2017.01) |
| *A61K 31/337* | (2006.01) |
| *A61P 35/00* | (2006.01) |
| *A61P 43/00* | (2006.01) |
| *A61K 9/14* | (2006.01) |

(52) U.S. Cl.
CPC ............ *A61K 31/7068* (2013.01); *A61K 9/14* (2013.01); *A61K 31/337* (2013.01); *A61K 47/42* (2013.01); *A61P 35/00* (2018.01); *A61P 43/00* (2018.01)

(58) Field of Classification Search
CPC .. A61K 31/7068; A61K 47/42; A61K 31/337; A61P 35/00
USPC .................................................. 514/39, 49
See application file for complete search history.

(56) References Cited

U.S. PATENT DOCUMENTS

| | | | |
|---|---|---|---|
| 3,116,282 A | 12/1963 | Hunter | |
| 3,243,425 A | 3/1966 | Whistler | |
| 4,211,773 A | 7/1980 | Lopez et al. | |
| 4,220,774 A | 9/1980 | Kuehne | |
| 4,803,272 A | 2/1989 | Anton et al. | |
| 5,811,408 A | 9/1998 | Yoshimura et al. | |
| 6,103,707 A | 8/2000 | Yamada et al. | |
| 6,147,058 A | 11/2000 | Yoshimura et al. | |
| 6,448,415 B1 | 9/2002 | Lee et al. | |
| 7,148,223 B2 | 12/2006 | Secrist, III et al. | |
| 7,285,572 B2 | 10/2007 | Shinagawa et al. | |
| 7,858,788 B2 | 12/2010 | Yoshida et al. | |
| 8,329,925 B2 | 12/2012 | Voigtlander et al. | |
| 8,420,831 B2 | 4/2013 | Voigtlander et al. | |
| 9,221,865 B2 | 12/2015 | Nakamura et al. | |
| 9,475,835 B2 | 10/2016 | Nakamura et al. | |
| 10,059,734 B2 | 8/2018 | Kuniyoshi et al. | |
| 10,093,645 B2 | 10/2018 | Nakamura et al. | |
| 10,385,089 B2 | 8/2019 | Kuniyoshi et al. | |
| 2002/0173482 A1 | 11/2002 | Ajani et al. | |
| 2003/0124054 A1 | 7/2003 | Toyohara et al. | |
| 2003/0138864 A1 | 7/2003 | Ishitsuka et al. | |
| 2005/0129611 A1 | 6/2005 | Toyohara et al. | |
| 2006/0142238 A1 | 6/2006 | McGuigan | |
| 2006/0263434 A1 | 11/2006 | Desai et al. | |
| 2009/0069263 A1 | 3/2009 | Damha et al. | |
| 2010/0272717 A1 | 10/2010 | Evans et al. | |
| 2011/0152542 A1 | 6/2011 | Voigtländer et al. | |
| 2013/0005991 A1 | 1/2013 | Voigtländer et al. | |
| 2013/0252918 A1 | 9/2013 | McGuigan | |
| 2014/0378409 A1 | 12/2014 | Fujita et al. | |
| 2015/0011499 A1 | 1/2015 | Baba | |
| 2015/0152131 A1 | 6/2015 | Nakamura et al. | |
| 2016/0024132 A1 | 1/2016 | Nakamura et al. | |
| 2016/0355497 A1 | 12/2016 | Takeda et al. | |
| 2016/0355536 A1 | 12/2016 | Ito et al. | |
| 2016/0362389 A1 | 12/2016 | Nakamura et al. | |
| 2017/0233429 A1 | 8/2017 | Kuniyoshi et al. | |
| 2018/0079770 A1 | 3/2018 | Ye et al. | |
| 2018/0327377 A1 | 11/2018 | Nakamura et al. | |
| 2018/0360865 A1 | 12/2018 | Tanisaka et al. | |
| 2020/0352973 A1 | 11/2020 | Janku | |
| 2020/0405752 A1 | 12/2020 | Yamada et al. | |

FOREIGN PATENT DOCUMENTS

| | | |
|---|---|---|
| CA | 2224155 C | 10/2004 |
| CN | 1615131 A | 5/2005 |
| CN | 101058557 A | 10/2007 |
| CN | 101200463 A | 6/2008 |
| CN | 101880287 A | 11/2010 |

(Continued)

OTHER PUBLICATIONS

Zajchowski et al. (Int. J. Cancer: 114, 1002-1009 (2005).*
Kolinsky et al. (Journal of Cancer Therapy, 2014, 5, 605-610).*
Shinji Miura, et al., "Comparison of 1-(2-deoxy-2-fluoro-4-thio-β-Darabinofuranosyl) cytosine with gemcitabine in its antitumor activity", Cancer Letters, vol. 144, pp. 177-182, (1999).
Daniel D. Von Hoff, M.D., et al., "Increased Survival in Pancreatic Cancer with nab-Paclitaxel plus Gemcitabine", The New England Journal of Medicine, Oct. 31, 2013, vol. 369, No. 18, pp. 1691-1703.
Shinji Miura, et al., "Potent antitumor effect of 1-(2-deoxy-2-fluoro-4-thio-β-Darabinofuranosyl) cytosine on peritoneal dissemination models of gastrointestinal cancers", Oncology Reports, vol. 9, pp. 1319-1322, (2002).

(Continued)

*Primary Examiner* — Shaojia A Jiang
*Assistant Examiner* — Michael C Henry
(74) *Attorney, Agent, or Firm* — Sughrue Mion, PLLC

(57) ABSTRACT

An object of the present invention is to provide an anti-tumor agent and an anti-tumor kit which have superior anti-tumor effect as compared with a therapy with gemcitabine, paclitaxel or a combination thereof; as well as an anti-tumor effect enhancer. According to the present invention, provided is an anti-tumor agent including paclitaxel or a salt thereof and 1-(2-deoxy-2-fluoro-4-thio-β-D-arabinofuranosyl)cytosine or a salt or prodrug thereof.

12 Claims, 2 Drawing Sheets

(56) References Cited

FOREIGN PATENT DOCUMENTS

| | | |
|---|---|---|
| CN | 101896177 A | 11/2010 |
| CN | 102166190 A | 8/2011 |
| CN | 104203969 A | 12/2014 |
| EP | 0 841 344 A1 | 5/1998 |
| EP | 2 799 070 A1 | 11/2014 |
| EP | 2 832 740 A1 | 2/2015 |
| EP | 2 883 866 A1 | 6/2015 |
| ER | 2 883 542 A1 | 6/2015 |
| JP | 53-119810 A | 10/1978 |
| JP | 55-49395 A | 4/1980 |
| JP | 56-92239 A | 7/1981 |
| JP | 5-178875 A | 7/1993 |
| JP | H06-501261 A | 2/1994 |
| JP | 8-53490 A | 2/1996 |
| JP | 8-504753 A | 5/1996 |
| JP | 10-282039 A | 10/1998 |
| JP | 2003-172990 A | 6/2003 |
| JP | 2005-503358 A | 2/2005 |
| JP | 2006-335737 A | 12/2006 |
| JP | 2006-528162 A | 12/2006 |
| JP | 2007-514643 A | 6/2007 |
| JP | 2008-530248 A | 8/2008 |
| JP | 4202327 B2 | 12/2008 |
| JP | 2009-538829 A | 11/2009 |
| JP | 2010-59173 A | 3/2010 |
| JP | 4719356 B2 | 7/2011 |
| JP | 2011-526242 A | 10/2011 |
| JP | 2013-514260 A | 4/2013 |
| JP | 2013/146833 | 10/2013 |
| JP | 2013-540129 A | 10/2013 |
| JP | 2014/027658 A1 | 2/2014 |
| RU | 2284184 C2 | 9/2006 |
| WO | 91/04982 A1 | 4/1991 |
| WO | 94/05687 A1 | 3/1994 |
| WO | 96/01834 A1 | 1/1996 |
| WO | 97/37993 A1 | 10/1997 |
| WO | 97/38001 A1 | 10/1997 |
| WO | 1997/038001 A1 | 10/1997 |
| WO | 97/49716 A1 | 12/1997 |
| WO | 99/28312 A2 | 6/1999 |
| WO | 99/43690 A1 | 9/1999 |
| WO | 02058740 A1 | 8/2002 |
| WO | 03/000200 A2 | 1/2003 |
| WO | 2004/014930 A1 | 2/2004 |
| WO | 2004/014931 A1 | 2/2004 |
| WO | 2004/027658 A1 | 4/2004 |
| WO | 2004/100891 A2 | 11/2004 |
| WO | 2004/106352 A1 | 12/2004 |
| WO | 2005/012327 A2 | 2/2005 |
| WO | 2006/073197 A1 | 7/2006 |
| WO | 2007/056596 A2 | 5/2007 |
| WO | 2007/068113 A1 | 6/2007 |
| WO | 2007/130783 A2 | 11/2007 |
| WO | 2011/074484 A1 | 6/2011 |
| WO | 2012/045999 A1 | 4/2012 |
| WO | 2013/100014 A1 | 7/2013 |
| WO | 2013/146833 A1 | 10/2013 |
| WO | 2014/027658 A1 | 2/2014 |
| WO | 2015/038596 A1 | 3/2015 |
| WO | 2016/068341 A1 | 5/2016 |
| WO | 2016/155593 A1 | 10/2016 |
| WO | 2017/150511 A1 | 9/2017 |
| WO | 2017/109444 A1 | 6/2018 |
| WO | 2019/176984 A1 | 9/2019 |

OTHER PUBLICATIONS

William J. Gradishar, et al., "Phase III Trial of Nanoparticle Albumin-Bound Paclitaxel Compared With Polyethylated Castor Oil-Based Paclitaxel in Women With Breast Cancer", Journal of Clinical Oncology, Nov. 1, 2005, vol. 23, No. 31, pp. 7794-7803.
International Search Report for PCT/JP2017/031074 dated Oct. 24, 2017 (PCT/ISA/210).
Written Opinion dated Oct. 24, 2017 in International Application No. PCT/JP2017/031074.
International Preliminary Report on Patentability with translation of the Written Opinion dated Mar. 5, 2019 in International Application No. PCT/JP2017/031074.
Office Action dated Aug. 20, 2019 issued by the Australian Intellectual Property Office in counterpart Australian application No. 2017319260.
Shinji Miura et al., "The Antitumor Mechanism of 1-(2-Deoxy-2-fluoro-4-thio-β-D-arabinofuranosyl)-cytosine: Effects of Its Triphosphate on Mammalian DNA Polymerases", Japanese Journal of Cancer Research, vol. 92, No. 5, pp. 562-567, May 2001, 6 pages total.
Extended European Search Report dated Aug. 7, 2019 issued by the European Patent Office in counterpart European application No. 17846534.0.
Office Action dated Oct. 14, 2019 from the Russian Patent and Trademark Office in Russian application No. 2019105574.
Office Action dated Dec. 23, 2019 from the Intellectual Property of India in Indian application No. 201947007839.
C. Khanna et al., "A Review of Paclitaxel and Novel Formulations Including Those Suitable for Use in Dogs", Journal of Veterinary Internal Medicine, vol. 29, 2015, pp. 1006-1012 (7 pages total).
D.A. Kharkevich, Pharmacology, Moscow, Meditsina, 1987, pp. 46-48 (3 pages total).
Mashkovskiy M.D., "Lekarstvennyye sredstva [Drugs]", 14-ed., vol. 1, Moscow, pp. 11, 2001 (2 pages total).
Office Action dated Jan. 21, 2020, from the Japanese Patent Office in Japanese Application No. 2018-537328.
Deborah Zajchowski et al., "Anti-tumor efficacy of the nucleoside analog 1-(2-deoxy-2-fluoro-4-thio-l3-D-arabinofuranosyl) cytosine (4'-thio-FAC) in human pancreatic and ovarian xenograft models.", Proc Amer Assoc Cancer Res, Apr. 2004, vol. 45, (5 pages total).
Anna Cividalli et al., "Enhancement of Radiation Response by Paclitaxel in Mice According to Different Treatment Schedules", International Journal of Radiation Oncology Biol. Phys., 1998, vol. 40, No. 5, pp. 1163-1170 (total 8 pages).
Wenger A., Pharmacological incompatibility, Bulletin of Siberian Medicine, 2003, n3, pp. 49-56 (total 8 pages).
Communication dated Mar. 26, 2020 from the Russian Patent Office in RU Application No. 2019105574/04.
Communication dated May 7, 2020 from the European Patent Office in EP Application No. 17846534.0.
American Association for Cancer Research (AACR) Annual Meeting, Apr. 1-5, 2017, Washington, DC (48 pages total).
Falchook et al., "First-in-human phase 1 trial of pyrimidine antimetabolite FF-10502-01 in patients with advanced cancer", AACR Annual Meeting, Apr. 4, 2017 (1 page total).
International Preliminary Report on Patentability dated Aug. 9, 2018 in International Application No. PCT/JP2018/007772, corresponding to U.S. Appl. No. 16/941,674.
International Search Report dated May 1, 2018 in International Application No. PCT/JP2018/007772, corresponding to U.S. Appl. No. 16/941,674.
Janku et al., "Preliminary Activity of FF-10502-01 in Patients with Refractory Advanced Cholangiocarcinoma", Annual Conference of cholangiocarcinoma foundation, Jan. 31, 2018, Salt Lake City, USA (1 page total).
Mima et al., "In vitro and in vivo evaluation of FF-10502-01, a new pyrimidine nucleoside analogue", AACR Annual Meeting, Apr. 5, 2017 (1 page total).
Miura et al., "Antitumor activity of a novel orally effective nucleoside, 1-(2-deoxy-2-fluoro-4-thio-B-D-arabinofuranosyl)cytosine", Cancer Letters, 1998, vol. 129, pp. 103-110 (8 pages total).
Saeki et al., "A novel antimetabolite, FF-10502-01 exhibits potent antitumor activity via inhibition of both DNA replication and DNA damage repair in solid tumor cells", AACR 2018 Abstract 3350, Apr. 15, 2018, Chicago, USA (1 page total).
Suzuki et al., "Evaluation of FF-10502-01, a new pyrimidine nucleoside analogue, in pancreatic (PANC) patient-derived xenograft (PDX) models compared to gemcitabine and in combination with nab-paclitaxel", AACR Annual Meeting, Apr. 5, 2017 (2 pages total).

(56) References Cited

OTHER PUBLICATIONS

Written Opinion of the International Searching Authority dated May 1, 2018 in International Application No. PCT/JP2018/007772, corresponding to U.S. Appl. No. 16/941,674.
International Search Report dated May 21, 2019 in International Application No. PCT/JP2019/010169, corresponding to U.S. Appl. No. 17/018,413.
Written Opinion of the International Searching Authority dated May 21, 2019 in International Application No. PCT/JP2019/010169, corresponding to U.S. Appl. No. 17/018,413.
Akamatsu et al., "Action mechanism of cancer phamiacotherapeutic agents, Cytotoxic antineoplastic agent, Platinum preparation, alkylating agent, and anticancer antibiotics", Japanese Journal of Clinical Medicine (special issue), 2014, vol. 27, suppl. 2, pp. 124-126.
Mima et al., "FF-10502, an Antimetabolite with Novel Activity on Dormant Cells, Is Superior to Gemcitabine for Targeting Pancreatic Cancer Cells", The Journal of Pharmacology and Experimental Therapeutics, 2018, vol. 366, No. 1, pp. 125-135.
Chikuma et al., "Current Status and Future Perspectives of Platinum Antitumor Drugs", Yakugaku Zasshi, 2008, vol. 128, No. 3, pp. 307-316.
Heinemann et al., "Randomized Phase III Trial of Gemcitabine Plus Cisplatin Compared With Gemcitabine Alone in Advanced Pancreatic Cancer", Journal of Clinical Oncology, 2006, vol. 24, No. 24, pp. 3946-3952 (13 pages total).
Poplin et al., "Phase III, Randomized Study of Gemcitabine and Oxaliplatin Versus Gemcitabine Kfixed-dose rate infusion) Compared With Gemcitabine (30-minute infusion) in Patients With Pancreatic Carcinoma E6201: A Trial of the Eastern Cooperative Oncology Group", Journal of Clinical Oncology, 2009, vol. 27, No. 23, pp. 3778-3785 (8 pages total).
Office Action dated Jul. 31, 2020, from the China National Intellectual Property Administration in corresponding Chinese Application No. 201780053185.4.
Zheng Baoguo, "Modern clinical oncology", Jilin Science and Technology Publishing House, Apr. 30, 2013, p. 558 (3 pages total).
Yu Yongqiang, "Modern hospital diagnosis and treatment routine (internal medicine, pediatrics)", Anhui Science and Technology Publishing House, Sep. 30, 2012, pp. 865-866 (4 pages total).
Office Action dated Aug. 25, 2020 from the Japanese Patent Office in corresponding Japanese Application No. 2018-537328.
U.S. Appl. No. 16/941,674, filed Jul. 29, 2020 (Janku).
U.S. Appl. No. 17/018,413, filed Sep. 11, 2020 (Yamada).
Office Action dated May 31, 2021 issued by the Taiwanese Patent Office in Taiwanese Application No. 106129543.
P. Ettmayer et al., "Lessons Learned from Marketed and Investigational Prodrugs", Journal of Medicinal Chemistry, vol. 47, No. 10, May 6, 2004, pp. 2393-2404 (12 pages total).
Non-Final Office Action dated Dec. 31, 2020 issued in U.S. Appl. No. 16/941,674.
Dilruba et al., "Platinum-based drugs: past, present and future", Cancer Chemother Pharmacol, 2016, vol. 77, pp. 1103-1124 (22 pages total).
Extended European Search Report dated Apr. 7, 2021 in European Application No. 19767269.4, corresponding to U.S. Appl. No. 17/018,413.
Office Action dated Mar. 30, 2021 in Australian Application No. 2018404329, corresponding to U.S. Appl. No. 16/941,674.
Office Action dated Mar. 31, 2021 in Canadian Application No. 3,035,334.
Yuichi Yoshimura et al., "A Facile, Alternative Synthesis of 4'-Thioarabinonucleosides and their Biological Activities", J. Med. Chem. 1997, 40(14); pp. 2177-2183.
Yuichi Yoshimura et al., A Novel Synthesis of 2'-Modified 2'-Deoxy-4'-thocytidines from D-Glucose1, J. Org. Chem., 1997, pp. 3140-3152, vol. 62.
Yuichi Yoshimura et al., "Synthetic Studies on 2'-Substituted-4'-Thiocytidine Derivatives as Antineoplastic Agents", Nucleosides & Nucleotides, 1999, pp. 815-820, vol. 18, Nos. 4&5.

Yuichi Yoshimura et al., "An alternative synthesis of antineoplastic nucleoside 4'-thioFAC", Nucleic Acids Symposium Series No. 39, 1998, pp. 11-12.
Yuichi Yoshimura et al., "An Alternative Synthesis of Antineoplastic 4'-Thiocytidine Analogue 4'-ThioFAC", Tetrahedron Letters, 1999, pp. 1937-1940, vol. 40.
Yuichi Yoshimura e al., "Synthesis and Biological Activities of 2'-Deoxy-2'fluoro-4'thioarabinofuranosylpyrimidine and -Purine Nucleosides", Bioorganic & Medicinal Chemistry, 2000, pp. 1545-1558, vol. 8.
Yoshimura et al., Synthesis of 2'-deoxy-2'-fluoro-4'-thioarabinonucleosides as potential antitumor and antiviral agents from D-glucose, Nucleic Acids Symposium Series, No. 35, pp. 15-16, 1996 (2 pages total).
Yoshimura et al., A Novel Synthesis of New Antineoplastic 2'-Deoxy-2'-substituted-4'-thiocytidines, Journal of Organic Chemistry, vol. 61, No. 3, pp. 822-823, 1996 (2 pages total).
Yoshimura et al. "An Alternative Synthesis of the Antineoplastic Nucleoside 4'-ThioFAC and Its Application to the Synthesis of 4'-ThioFAG and 4'-Thiocytarazid", J.Org Chern., vol. 64, Jun. 14, 1999, pp. 7912-7920 (9 pages total).
Y. Yoshimura et al., Nucleic Acids Symposium Series, No. 35, pp. 15-16 (1996).
Y. Yoshimura et al., Journal of Organic Chemistry, vol. 61, No. 3, pp. 822-823 (1996).
Wu-Bao Wang et al., "A Practical Synthesis of Sugar-Derived Cyclic Nitrones: Powerful Synthons for the Synthesis of Iminosugars", Synlett, 2010, pp. 488-492, No. 3.
Written Opinion for PCT/JP2015/080885, dated Feb. 2, 2016.
William Plunkett et al., "Preclinical characteristics of gemcitabine", Anti-Cancer Drugs, 1995, pp. 7-13, vol. 6, Suppl. 6.
Watts et al., "2'-Fluoro-4'-thioarabino-modified oligonucleotides: conformational switches linked to siRNA activity" Nuclei. Acids Res. (2007) vol. 35(5), pp. 1441-1451.
Watts et al., "Synthesis and Conformational Analysis of 2'-Fluoro-5-methyl-4'-thioarabinouridine (4'S-FMAU)", Journal of Organic Chemistry, vol. 71, No. 3, Jan. 22, 2006, pp. 921-925, XP002606716.
Wang et al. "A Practical Synthesis of Sugar-Derived Cyclic Nitrones: Powerful Synthons for the Synthesis of Iminosugars", Synlett Letter, 2010, No. 3, pp. 488-492 (5 pages total)93.
Vorbruggen et al., "Synthesis of nucleosides" Org. Reactions (2000), p. 55.
Vjera Pejanovic et al., "Synthesis and Biological Evaluation of Some Novel 4'-Thio-L-ribonucleosides with Modified Nucleobase Moieties", Bioorganic & Medicinal Chemistry Letters, 2003, 13(11) pp. 1849-1852.
Zefirova, O.N., et al., "On history of emergence and development of bioisoterism concept", Moscow University Herald, Series 2, Chemistry, 2002, T. 43, No. 4, pp. 251-256 (6 pages).
Ototani et al., "Preparation and Antitumor Activity of 4'-Thio Analogs of 2,2,-Anhydro-1-β-D-arabinofuranosylcytosine," Journal of Medicinal Chemistry, 1974, vol. 17, No. 5, pp. 535-537 (3 pages total).
Thomas B. Mercer et al., Looking glass inhibitors: both enanthiomeric N-benzyl derivatives of 1,4-dideoxy-1,4-imino-D-lyxitol [a potent competitive inhibitor of a-D-glactosidase ] and of 1-4-dideoxy-1,4-imino-L-lyxitol [a weak competitive inhibitor of a-D-glactosidase] inhibit naringinase, an α-L-rhamnosidase competitively, Tetrahedron: Asymmetry, 2009, pp. 2368-2373, vol. 20, No. 20.
Tann et al., Fluorocarbohydrates in Synthesis. An Efficient Synthesis of 1-(2-Deoxy-2-fluoro-ß-D-arabino-furanosyl)-5-iodouracil (ß-FIAU) and 1-(2-Deoxy-2-fluoro-ß-D-arabinofuranosyl) thymine (ß-FMAU), Journal of Organic Chemistry, American Chemical Society, vol. 50, No. 19, 1985. pp. 3644-3647 (4 pages total).
Takashi Komine et al., "Synthesis and Structure-Activity Relationship Studies of Highly Potent Novel Oxazolidinone Antibacterials", J. Med. Chem., 2008, pp. 6558-6562, 2008, vol. 51, No. 20.
Stephen M. Berge et al., "Pharmaceutical Salts", Journal of Pharmaceutical Sciences, Jan. 1977, pp. 1-19, vol. 66, No. 1.
Stephanie A. Hartsei et al., "Synthesis of 9-(4-Thioxylofuranosyl) adenine via a Novel Glycosylation Reaction", Tetrahedron Letters 39 (1998) pp. 205-208.

(56) References Cited

OTHER PUBLICATIONS

Shinji Miura et al., "Potent antitumor effect of 1-(2-deoxy-2-fluoro-4-thio-β-D-arabinofuransoyl)cytsine on peritoneal dissemination models of gastrointestinal cancers", Oncology Reports, 2002, pp. 1319-1322, vol. 9, No. 6.
Shinji Miura et al., "Comparison of 1-(2-deoxy-2fluoro-4-thio-β-D-arabinofuranosyl)cytosine with gemcitabine in its antitumor activity", Cancer Letters, 1999, pp. 177-182, vol. 144.
Shinji Miura et al., "Antitumor activity of a novel orally effective nucleoside, 1-(2-deoxy-2-fluoro-4-thio-β-D-arabinofuranosyl)cytosine", Cancer Letters, 1998, pp. 103-110, vol. 129.
Russian Office Action for Application No. 2015108790, dated Apr. 25, 2016.
Ronald C. Horton Jr. et al., "Aldehyde-Terminated Self-Assembled Monolayers on Gold: Immobilization of Amines onto Gold Surfaces", J. Am. Chem. Soc., 1997, vol. 119; pp. 12980-12981.
Raoul, S., et al., "1H, 13C and 15N Nuclear magnetic resonance analysis and chemical features of the two main radical oxidation products of 2'-'deoxyguanosine: oxazolone and imidazolone nucleosides", J. Chemical So., Perkin Trans. 2, 1996, Issue 3, pp. 371-381 (11 pages).
R. M. Rowell et al., "Derivatives of a-D-Glucothiopyranose", J. Org. Chem., 1996, vol. 31; pp. 1514-1516.
Peter Haeberli et al., "Syntheses of 4,-thioribonucleosides and thermodynamic stability and crystal structure of RNA oligomers with incorporated 4'-thiocytosine," Nucleic Acids Research, 2005, vol. 33, No. 13; pp. 3965-3975.
PCT International Preliminary Report on Patentability (IPRP), dated Jun. 19, 2012 for PCT International Application No. PCT/JP2010/072182.
Paul Karrer, "Organic Chemistry", 2nd English Edition, Elsevier Publ. Comp., Inc., NY, pp. 92-102 (1946).
Partial Supplemental European Search Report issued in European Application No. 13879640.4, dated Feb. 16, 2016.
Partial European Search Report dated Nov. 24, 2010 issued in European Application No. 10163406.
Ototani et al., "Preparation and Antitumor Activity of 4'-Thio Analogs of 2/2'-Anhydro-1-β-D-arabinofuranosylcytosine," Journal of Medicinal Chemistry, 1974, vol. 17, Nos. pp. 535-537 (3 pages total).
Oscar Varela et al., "First Synthesis of Aldopentono-1,4-thiolactones", J. Org. Chem., 1993, pp. 7860-7864, vol. 58, No. 27.
Official Action dated Sep. 13, 2016 issued in Israeli patent application No. 234222.
Official Action dated Oct. 5, 2015 issued in Australian patent application No. 2013241341.
Official Action dated Jan. 11, 2017 issued in Korean Patent Application No. 10-2015-7003655 with its English machine translation.
Official Action dated Jan. 16, 2017 issued in Chinese Patent Application No. 201380042642.1.
Official Action dated Jan. 28, 2015 issued in New Zealand Patent Application No. 701245.
Official Action dated July 1, 2015 issued in Chinese patent application No. 201380016308.9.
Official Action dated Mar. 19, 2015 issued in Singapore Patent Application No. 11201406080V.
Official Action dated Mar. 21, 2016 issued in Russian Patent Application 2014143277/04.
Official Action dated Mar. 29, 2016 issued in Canadian Patent Application No. 2,865,742.
Official Action dated May 25, 2016 issued in Taiwanese Patent Application No. 102110915.
Official Action dated Nov. 2, 2015 issued in Canadian Patent Application No. 2,880,794.
Official Action dated Nov. 5, 2015 issued in Russian Patent Application No. 2014143277.
Official Action dated Oct. 25, 2016 issued in Korean patent application No. 10-2014-7030209.
Office Action issued in Korean application No. 10-2012-7018741 dated Dec. 1, 2016.
Office Action issued in Russian application No. 2012130422 dated Jan. 22, 2015.
Office Action issued in Singapore application No. 2012044368 dated Jun. 11, 2014.
Office Action issued in Vietnamese application No. 1-2012-02041 dated Jul. 4, 2013.
Office Action issued in Vietnamese application No. 1-2012-02041 dated Mar. 7, 2014.
Office Action dated Aug. 11, 2016 in U.S. Appl. No. 14/498,334.
Office Action dated Nov. 8, 2012 in U.S. Appl. No. 13/606,746 (now U.S. Pat. No. 8,420,831).
Official Action dated Apr. 7, 2015 issued in Japanese Patent Application No. 2014-507938.
Official Action dated Sep. 30, 2016 issued in Taiwanese patent application No. 102110915.
Official Action dated Aug. 18, 2016 issued in Canadian Patent Application No. 2,880,794.
Official Action dated Aug. 21, 2015 issued in New Zealand patent application No. 701245.
Official Action dated Dec. 29, 2016 issued in Russian Patent Application No. 2015108790.
Notice of Allowance dated Feb. 15, 2017 in U.S. Appl. No. 14/498,334.
Notice of Allowance issued in U.S. Appl. No. 14/873,966, dated May 26, 2016.
Notice of Final Rejection dated Apr. 3, 2017 issued in Korean patent application No. 10-2014-7030209.
Notice of Final Rejection dated Nov. 21, 2016 issued in Korean Patent Application No. 10-2015-7003655.
Notices of Allowance and Allowability dated Nov. 8, 1999, in U.S. Appl. No. 08/973,529 (now U.S. Pat. No. 6,147,058).
Office Action in Taiwanese U.S. Appl. No. 99/142,198 dated Sep. 11, 2014.
Office Action issued in Australian application No. 2010331367 dated Jul. 25, 2016.
Office Action issued in Canadian application No. 2,784,399 dated Oct. 6, 2016.
Office Action issued in Chinese application No. 201380042642.1 dated Aug. 2, 2017.
Office Action issued in European application No. 10801279.0 dated Dec. 16, 2013.
Office Action issued in European application No. 10801279.0 dated Jun. 4, 2013.
Office Action issued in European application No. 14177042.0 dated Aug. 19, 2015.
Martin W. Bredenkamp et al., "Stannylene Directed Selective Acylation of Some Open-Chain L-Arabinose Derivatives", Tetrahedron Letters, 1990, 31(19) pp. 2759-2762.
Masajiro Kawana et al., "The Synthesis of 2',3'-Diodexycytidene and Its 2'-Azido Analogue Applications of the Deoxygenative [1,2]-Hydride Shift of Sulfonates with Mg(OMe)2-NaBH4", Chemistry Letters, 1987, pp. 2419-2422.
Mayumi Takahashi et al., "Synthesis and crystal structure of 20-deoxy-20-fluoro-40-thioribonucleosides: substrates for the synthesis of novel modified RNAs", Tetrahedron, 2008, pp. 4313-4324, vol. 64.
Miura et al., "Suppression of Peritoneal Dissemination by 4'-thio-FAC," Oncology Reports, vol. 9, No. 6, Nov.-Dec. 2002, pp. 1319-1322 (9 pages total).
Naveen K. Khare et al., "Synthesis of 4-deoxy-4-thioarabinofuranosyl disaccharides, analogs of Mycobactrial arabinoglactan", Indian Journal of Chemistry, Nov. 2008, pp. 1748-1752, vol. 47B.
Office Action issued in U.S. Appl. No. 14/873,966, dated Feb. 8, 2016.
Office Action issued in U.S. Appl. No. 14/621,119, dated Mar. 24, 2015.
Notice of Allowance dated Aug. 30, 2012 in U.S. Appl. No. 12/959,735 (now U.S. Pat. No. 8,329,925).
Larry W. Hertel et al., "Evaluation of the Antitumor Activity of Gemcitabine (2',2'-Difluoro-2'-deoxycytidine)", Cancer Research, Jul. 15, 1990, pp. 4417-4422, vol. 50.
Magdalena Slusarczyk et al., "Application of ProTide Technology to Gemcitabine: A Successful Approach to Overcome the Key

(56) References Cited

OTHER PUBLICATIONS

Cancer Resistance Mechanisms Leads to a New Agent (NUC-1031) in Clinical Development", J. Med. Chem, 2014, pp. 1531-1542, vol. 57.
Koen Vanhessche et al., "L-Ribulose A: Novel Chiral Pool Compound", Tetrahedron Letters, pp. 2337-2340, 1990, vol. 3, No. 16.
Office Action for Korean Application No. 10-2015-7003655, dated May 12, 2016.
Lak Shin Jeong et al., "N6-Substituted D-4'-Thioadenosine-5'-methyluronamides: Potent and Selective Agonists at the Human A3 Adenosine Receptor", J. Med. Chem., 2003, pp. 3775-3777, vol. 46, No. 18.
Karrer, Org. Chem. 2nd Ed. (1996), pp. 92-102.
King, "Bioisosteres, Conformational Restriction, and Pro-drugs—Case History: An Example of a Conformational Restriction Approach," Med. Chem., Principle and Practice (1994), pp. 206-208, Chapter 14.
Karmal N. Tiwari et al., "Synthesis and Biological Activity of 4'-Thio-L-Xylofuranosyl Nucleosides", Nucleosides, Nucleotides & Nucleic Acids, 2001, pp. 743-746, vol. 20 Nos. 4-7.
Kamal N. Tiwari et al., "The Synthesis and Biological Activity of 1-(2-Deoxy-4-Thio-α-L-Threo-Pentofuranosyl)Thymine", Nucleosides & Nucleotides, 12(8), pp. 841-846 (1993).
Kamal N. Tiwari et al., "Synthesis and Anti-Cancer Activity of Some Novel 5-Azacytosine Nucleosides", Nucleosides, Nucleotides & Nucleic Acids, 2003, 22(12), pp. 2161-2170.
Junji Fujita et al., "Synthesis of thiosaccharides employing the Pummerer rearrangement of tetrahydrothiopyran oxides", Tetrahedron 2004, vol. 60, No. 32, pp. 6829-6851.
Johan Fanton e al., "Enzymatic and Organocatalyzed Asymmetric Aldolization Reactions for the Synthesis of Thiosugar Scaffolds", European Journal of Organic Chemistry, 2012 pp. 203-210.
John A. Secrist III et al. "Synthesis and Biological Activity of 2'-Deoxy-4'-thio Pyrimidine Nucleosides", J. Med. Chem. 1991, 34, No. 8 (pp. 2361-2366).
Jeong, et al., The Stereochemical Outcome of the DAST Fluorination of 4'-Thipyrimidine Nucleosides with "Up" Hydroxyl Groups is Controlled by the Oxidation State of the Sulfur Atom, Chemistry Letters, pp. 301-302, 1995. (2 pages total).
Jeong et al., Unanticipated Retention of Configuration in the DAST Fluorination of Deoxy-4'-thiopyrimidine Nucleosides with "Up" Hydroxyl Groups. Tetrahedron Letter, vol. 35, No. 41, pp. 7569-7572, 1994. (4 pages total).
Jeong et al., Tetrahedron Letters, 35(41):7569-7572, 1994.
Jeong et al., Tetrahedron Letters, 35(41):7573-7576, 1994.
Jeong et al., Facile Fluorination of Deoxy-4'-thiopyrimidine Nucleosides with "Down" Hydroxyl Groups. Retention of Configuration After Fluoride Opening of the Quartenized N3-MEM Anhydronucleosides, Tetrahedron Letters, vol. 35, No. 41, pp. 7573-7576,1994 (4 pages total).
Jeong, et al., Participation of sulfur occurred during the Mitsunobu reaction: synthesis of novel isodideoxythionucleosides, J. Chem. Soc., Perkin Trans. 1, pp. 3325-3326, 1998 (2 pages total).
J. Allen Miller et al., "2,2'-Anhydro-4'-Thionucleosides: Precursors for 2'-Azido- and 2'-Chloro-4'-thionucleosides and for a Novel Thiolane to Thietane Rearrangement", Nucleosides, Nucleotides and Nucleic Acids, vol. 19, No. 9, Sep. 24, 2000, pp. 1475-1486, XP055207502.
Office Action for Japanese Application No. 2014-563560 dated Mar. 1, 2016.
Jean-Baptiste et al. "Synthesis of 2',3'-Dideoxy-2'-Fluoro-4'-Thionucleosides from a Fluoroxanthate", Synlett, Jan. 8, 2008, No. 6, pp. 817-820 (5 pages total).
International Search Report and Written Opinion for PCT/JP2013/058896, dated Jun. 4, 2013.
International search Report for PCT/JP2015/080885, dated Feb. 2, 2016.
International Search Report issued in PCT/JP2013/071871, dated Nov. 26, 2013.

International Preliminary Report on Patentability and Translation of Written Opinion dated Oct. 9, 2014 from the International Bureau in International application No. PCT/JP2013/058896.
International Preliminary Report on Patentability with a Translation of Written Opinion issued from the International Bureau in International Application No. PCT/JP2015/080885, dated May 11, 2017.
International Search Report and Written Opinion for PCT/JP2010/072182, dated Apr. 29, 2011.
International Preliminary Report on Patentability and Written Opinion of the International Searching Authority (forms PCT/IB388, PCT/373, PCT/ISA 237 and PCT/IB/326), dated Feb. 26, 2015, for International Application No. PCT/JP2013/071871, along with English translation.
Hyunah Choo et al., "Synthesis, Anti-HIV Activity, and Molecular Mechanism of Drug Resistance of L-2',3,-Didehydro-2,,3,-dideoxy-2,-fluoro-4'-thionucleosides", J. Med. Chem., 2003, pp. 389-398, vol. 46, No. 3.
Hiroshi Satoh et al., "Synthesis of L-Enantiomers of 4' • Thioarabinofuranosyl Pyrimidine Nucleosides", Bioorganic & Medicinal Chemistry Letters 8 (1998) pp. 989-992.
Hua Lin et al., "Highly Efficient Asymmetric Synthesis of Enantiopure Dihydro-1,2-oxazines: Dual-Organocatalyst-Promoted Asymmetric Cascade Reaction", Organic Letters (2012), vol. 14, No. 15; pp. 3818-3821.
Houssine Ait-sir et al., "Synthesis and configurational assignments of 3-substituted 2-deoxy-4-thio-Derythro-pentofuranose derivatives", Journal of the Chemical Society, Perkin transactions 1,1996; No. 14 pp. 1665-1671.
Hayato Fujita et al., "Gene Expression Levels as Predictive Markers of Outcome in Pancreatic Cancer after Gemcitabine-Based Adjuvant Chemotherapy1,2", Neo Plasia, Oct. 2010, pp. 807-817, vol. 12, No. 10.
Hironobu Hashimoto et al., "Novel conversion of aldopyranosides into 5-thioaldopyranosides via acyclic monothioacetals with inversion and retention of configuration at C-5", Carbohydrate Research, vol. 282, Issue 2 (Feb. 23, 1996) pp. 207-221.
G. Inguaggiato et al., "Novel Triazole 2,-Deoxy-4-Thionucleosides: Stereoselective Synthesis and Biological Evaluation", Nucleosides & Nucleotides, 1999; vol. 18, No. 3; pp. 457-467.
Extended European Search Report (EESR) dated Oct. 12, 2015 issued in European patent application No. 13770090.2.
Extended European Search Report dated Mar. 16, 2017 issued in European Patent Application No. 17150141.4.
Extended European Search Report for Application No. 13879640.4 dated May 18, 2016.
Feng Zheng et al., "Synthesis of L-B-3'Deoxy-2',3'-difluoro-4'-thionucleosides", Organic Letters, 2006, pp. 6083-6086, vol. 8, No. 26.
Elmer J. Reist et al., "Synthesis the 4-Thio-D-and-L-Ribofuranose and the Corresponding Adenine Nucleosides", Journal of the American Chemical Society, 1964, 86(24), pp. 5658-5663.
Eva Bozo et al., "Synthesis of 4-cyanophenyl and 4-nitrophenyl 1,5-dithio-L-and -D-arabinopyranosides possessing antithrombotic activity[1,2]", Carbohydrate Research 1998, vol. 311; pp. 191-202.
Elmer J. Reist et al., "Thio Sugars, Synthesis of the Adenine Nucleosides of 4-Thio-D-Xylose and 4-Thio-D-Arabinose", Journal of Organic Chemistry, 1968, 33(1) pp. 189-192.
Extended European Search Report (EESR) issued in European application No. 14177042.0 dated Oct. 2, 2014.
Extended European Search Report (EESR) issued in application No. 15853887.6 dated Aug. 17, 2017.
Deborah A. Zajchowski et al., "Anti-tumor efficacy of the nucleoside analog 1-(-deoxy-2-fluoro-4-thio-B-D-arabinofuranosyl) cytosine (4'-thio-FAC) on human pancreatic and ovarian tumor xenograft models", Int. J. Cancer, 2005, pp. 1002-1009, vol. 114.
Dusan Miljkovic et al., "An improved synthesis of methyl S-thio-D-arabino-pyranosides", Journal of the Serbian Chemical Society, vol. 55, 1990; pp. 359-361.
David A. Berges et al.5 "Bicyclic diazasugars. Part 3: 6-D-Mannose and 6-deoxy-6-L-gulose analogues", Tetrahedron, 2001, vol. 57; pp. 9915-9924.

(56) References Cited

OTHER PUBLICATIONS

Cottrell et al. "Reactions of Sugar Chlorosulfates", Canadian Journal of Chemistry, Jul. 1, 1966, vol. 44, No. 13, pp. 1483-1491 (9 pages total).
Cox, J.M., et al., "Cyclic Hemithioacetals: Analogues of Thiosugars with Sulphur in the Ring", J. Chem. Soc., Section C, 1967, pp. 1130-1134.
Communication dated Sep. 12, 2016 from the U.S. Patent and Trademark Office in U.S. Appl. No. 14/873,966.
Communication dated Nov. 30, 2015 from the U.S. Patent and Trademark Office in U.S. Appl. No. 14/621,119.
Communication dated May 8, 2017, from the European Patent Office in European application No. 13879640.4.
Corrected Notice of Allowability dated Nov. 17, 2017 from the United States Patent and Trademark Office in U.S. Appl. No. 14/498,334.
Communication dated May 19, 2017, issued from the Europe Patent Office in European Patent Application No. 13770090.2.
Communication dated Mar. 28, 2017 from the European Patent Office in European Application No. 15751531.3.
Office Action dated Mar. 22, 2018, issued by the Korean Intellectual Property Office in Korean Application No. 10-2017-70183372.
Office Action dated Mar. 27, 2018 from the Intellectual Property Office of India in Application No. 1391/CHENP/2015.
Communication dated Jun. 14, 2017 from the State of Israel Patent Office in application No. 237086.
Communication dated Mar. 13, 2017 from the U.S. Patent and Trademark Office in U.S. Appl. No. 15/238,232.
Communication dated Jan. 31, 2017 from the European Patent Office in application No. 15751503.2.
Communication dated Jul. 2, 2015 from the U.S. Patent and Trademark Office in U.S. Appl. No. 14/621,119.
Communication dated Apr. 4, 2017 from the Japanese Patent Office in Japanese Application No. 2014029978.
Communication dated Jan. 23, 2018 from the Japanese Patent Office in application No. 2016-556227.
Office Action dated Apr. 12, 2018 from the Canadian Patent Office in Canadian application No. 2966138.
Communication dated Apr. 18, 2017 from the Japanese Patent Office in application No. 2016-504110.
Office Action dated Apr. 28, 2018 from the Russian Patent Office in Russian application No. 2017114338/04.
Communication dated Apr. 26, 2017, issued from the Mexico Patent Office in Mexican Patent Application No. MX/a/2014/011182.
Attardo, G., et al., "Efficient Synthesis of 5,8-Disubstituted-1,4-Dihydrobenzoxathiin-3-Oxides and Their Isomeric Structures, 4,7-Disubstituted-1,3-Dihydrobenzo[b] Thiophene-2,2-Dioxides", Tetrahedron Letters, vol. 35, No. 27, 1994, pp. 4743-4746 (4 pages).
Australian Office Action of Application No. 213303534 dated Dec. 1, 2015.
Chia-Lin J. Wang et al., "Synthesis of 2'(S), 3'(R), 5'-Trihydroxypentyladenine", Tetrahedron letters, 1988, pp. 1107-1110, vol. 29, No. 10.
Chinese Office Action for Application No. 201380042642.1, dated Nov. 2, 2015.
Abu T.M. Serajuddin, "Salt formation to improve drug solubility", Advanced Drug Delivery Reviews, 2007, pp. 603-616, vol. 59, No. 7.
Office Action dated Mar. 13, 2017, which issued during the prosecution of U.S. Appl. No. 15/238,784.
Office Action dated May 12, 1999, which issued during the prosecution of U.S. Appl. No. 08/973,529.
Gura et al., Systems for identifying new drugs are often faulty, Science, 278:1041-1042, 1997.
Johnson et al., Relationships between drug activity in NCI preclinical in vitro and in vivo models and early clinical trials, British Journal of Cancer, 84(10): 1424-1431,2001.
Pearce et al., Failure modes in anticancer drug discovery and development, Cancer Drug Design and Discovery, Edited by Stephen Neidle, Chapter 18, pp. 424-435 (2008).
Simone, Oncology; Introduction, Cecil Textbook of Medicine, 20th Edition, vol. 1, pp. 1004-1010, 1995.
International Search Report, issued by International Searching Authority dated May 19, 2015, in International Application No. PCT/JP2015/054305.
International Preliminary Report on Patentability issued from the International Bureau in International Application No. PCT/JP2015/054305, dated Jan. 4, 2016.
International Search Report, issued by International Searching Authority in International Application No. PGT/JP2015/052304, dated Mar. 10, 2015.
H. Driguez et al., "A Novel Synthesis of S-Thio-D-Glucose", Tetrahedron Letters, 1981, vol. 22, No. 50, pp. 5061-5062.
International Preliminary Report on Patentability issued from the International Bureau in International Application No. PCT/JP2015/052304, dated Feb. 16, 2016.
David Baker et al., "Large-scale preparation of D-allose: observations on the stereoselectivity of the reduction of 1,2:5,6-di-O-isopropylidene-α-D-ribo-hexofuranos-3-ulose hydrate", Carbohydrate Research, 1972, pp. 192-197, vol. 24.
Office Action dated May 19, 2017, issued from the Canadian Patent Office in Canadian Patent Application No. 2,880,794.
Office Action dated Oct. 27, 2017, from Intellectual Property India in Indian Patent Application No. 6251/CHENP/2012.
Office Action dated Sep. 26, 2017 from the Japanese Patent Office in Japanese Application No. 2016-136575.
Communication dated Sep. 3, 2018 from the Korean Intellectual Property Office in application No. 10-2016-7036051.
Communication dated Sep. 20, 2018 from the Korean Intellectual Property Office in application No. 10-2017-7018337.
Communication dated Jul. 3, 2018, issued by the European Patent Office in European Patent Application No. 17150141.4; 3 pages.
Communication dated May 30, 2018 issued by the Intellectual Property Office of Indonesia in Application No. W00201202819; 4 pages.
Journal of Medical Chemistry, Jan. 28, 2014, vol. 57, No. 4, Abstract (total 1 page).
Communication dated Jan. 29, 2019 from the Intellectual Property India in Indian Application No. 201747015114.
Feng Zheng et al., "Synthesis of L-β-3'-Deoxy-3', 3'-difluoro-4'-thionucleosides", Organic Letters, vol. 8, No. 26, pp. 6083-6086, 2006, 4 pages total.
Office Action dated Apr. 17, 2019, issued by the State Intellectual Property Office of People's Republic of China in Chinese Application No. 201610838593.8, corresponding to subject-matter related U.S. Appl. No. 16/045,047.
Communication dated Mar. 5, 2019 from the Taiwanese Patent Office in TW Application No. 104135717.
Communication dated Jun. 20, 2019, issued by the Mexican Patent Office in Mexican Application No. MX/a/2017/008865.
Office Action dated Sep. 15, 2020 in New Zealand Application No. 751051.
International Preliminary Report on Patentability dated Sep. 15, 2020 in International Application No. PCT/JP2019/010169.
Communication dated Nov. 25, 2020 from the European Patent Office in European Application No. 17846534.0.
Office Action dated Apr. 13, 2021 from the New Zealand Intellectual Property Office in corresponding NZ Application No. 751051.
Notice of Allowance dated Apr. 15, 2021 in U.S. Appl. No. 16/941,674.
Razumilava et al., "Cholangiocarcinoma", Lancet, 2014, vol. 383, pp. 2168-2179 (12 pages total).
Office Action dated Mar. 12, 2021 from the China National Intellectual Property Administration in corresponding CN Application No. 201780053185.4.
Yoshimura et al. "An Alternative Synthesis of the Antineoplastic Nucleoside 4'-ThioFAC and Its Application to the Synthesis of 4'-ThioFAG and 4'-Thiocytarazid", J.Org Chem., vol. 64, Jun. 14, 1999, pp. 7912-7920 (9 pages total).
Thomas B. Mercer et al., Looking glass inhibitors: both enanthiomeric N-benzyl derivatives of 1,4-dideoxy-1,4-imino-D-lyxitol [a potent competitive inhibitor of a-D-glactosidase ] and of 1-4-dideoxy-1,4-imino-L-lyxitol [a weak competitive inhibitor of a-D-glactosidase]

(56) References Cited

OTHER PUBLICATIONS inhibit naringinase, an a-L-rhamnosidase competitively, Tetrahedron: Asymmetry, 2009, pp. 2368-2373, vol. 20, No. 20.
Stephanie A. Hartsel et al., "Synthesis of 9-(4-Thioxylofuranosyl) adenine via a Novel Glycosylation Reaction", Tetrahedron Letters 39 (1998) pp. 205-208.
Official Action dated Jul. 1, 2015 issued in Chinese patent application No. 201380016308.9.
Notice of Allowance issued in U.S. Appl. No. 14/873,966, mailed on May 26, 2016.
Office Action in Taiwanese application No. 99142198 dated Sep. 11, 2014.
International Search Report issued in PCT/JP2013/0711871, dated Nov. 26, 2013.
Chinese Office Action for Application No. 201280042642.1, dated Nov. 2, 2015.
Office Action dated Jun. 6, 2021 by the Israeli Patent Office in Israeli Application No. 265044.
Notice of Reasons for Refusal dated Jul. 13, 2021 by the Japanese Patent Office in Japanese Application No. 2020-506583.
Office Action dated Oct. 26, 2021 in Japanese Application No. 2018-537328, corresponds to U.S. Appl. No. 16/286,930 (the present application).
Office Action dated Nov. 16, 2021 in Japanese Application No. 2020-193081, corresponds to U.S. Appl. No. 16/286,930 (the present application).
Office Action dated Dec. 8, 2021 in Australian Application No. 2019233338, corresponds to U.S. Appl. No. 17/018,413.
Office Action dated Nov. 22, 2021 in Taiwanese Application No. 106129543, corresponds to U.S. Appl. No. 16/286,930 (the present application).
Office Action dated Nov. 8, 2021 in Canadian Application No. 3,093,794, corresponds to U.S. Appl. No. 17/018,413.
Office Action dated Sep. 2, 2021 in Canadian Application No. 3,089,728, corresponds to U.S. Appl. No. 16/941,674.
Aman U. Buzdar et al., "Evaluation of Paclitaxel in Adjuvant Chemotherapy for Patients with Operable Breast Cancer: Preliminary Data of a Prospective Randomized Trial", Clinical Cancer Research, 2002, vol. 8, pp. 1073-1079 (8 pages total).
Hearing Notice dated Aug. 24, 2021 in Indian Application No. 201947007839.
Office Action dated Jul. 27, 2021 in Mexican Application No. MX/a/2019/002430.
Office Action dated Aug. 9, 2021 in Chinese Application No. 201780053185.4.
Office Action dated Sep. 3, 2021 in Australian Application No. 2019233338, corresponding to subject matter-related U.S. Appl. No. 17/018,413.
Office Action dated Sep. 27, 2021 in Brazilian Application No. BR112019003946-5.
Office Action dated Jan. 25, 2022 in Mexican Application No. MX/a/2019/002430.

* cited by examiner

ANTI-TUMOR AGENT, ANTI-TUMOR EFFECT ENHANCER, AND ANTI-TUMOR KIT

CROSS-REFERENCE TO RELATED APPLICATIONS

This application is a Continuation of PCT International Application No. PCT/JP2017/031074 filed on Aug. 30, 2017, which claims priority under 35 U.S.C. § 119(a) to Japanese Patent Application No. 2016-169167 filed on Aug. 31, 2016. Each of the above application(s) is hereby expressly incorporated by reference, in its entirety, into the present application.

BACKGROUND OF THE INVENTION

1. Field of the Invention

The present invention relates to an anti-tumor agent, an anti-tumor effect enhancer, and an anti-tumor kit.

2. Description of the Related Art

It is known that 1-(2-deoxy-2-fluoro-4-thio-β-D-arabinofuranosyl)cytosine (hereinafter, sometimes referred to as "Compound A") has excellent anti-tumor activity and is therefore useful as an anti-tumor agent (WO1997/038001A). It is also known that Compound A has potent anti-tumor activity also in the case of oral administration thereof to mice (Cancer Letters, 1999, Vol. 144, pp. 177 to 182, and Oncology Reports, 2002, Vol. 9, pp. 1319 to 1322). A salt of Compound A and a method for producing the same are also known (WO2013/146833A, WO2011/074484A, and WO2014/027658A).

In chemotherapy of malignant tumors, taxane-based anti-tumor agents such as paclitaxel and nab-paclitaxel are also used as useful drugs. However, it is known that the response rate to tumor with a taxane-based anti-tumor agent alone is as low as 10% to 25%, and the survival period of cancer patients is short (survival period of 12 to 15 months) (Journal of Clinical Oncology, 2005, Vol. 23, pp. 7794 to 7803).

In a clinical setting, a multidrug combination therapy has been carried out for the purpose of compensating for differences in susceptibility of each anti-tumor agent to tumor and of enhancing the drug efficacy, and a medicine combining paclitaxel and other drugs is also known (WO2013/100014A). For example, combination use of gemcitabine and nab-paclitaxel to pancreatic cancer patients has a response rate of 23% and a median survival period of 8.5 months (New England Journal of Medicine, 2013, Vol. 369, pp. 1691 to 1703), which cannot be said that the therapeutic effect is sufficiently high.

SUMMARY OF THE INVENTION

In recent years, a combination therapy has been widely carried out rather than administering an anti-tumor agent alone. However, it is completely unknown whether any anti-tumor effect will be enhanced or the effect will be offset in the case where any anti-tumor agents are used in combination.

An object of the present invention is to provide an anti-tumor agent and an anti-tumor kit which have superior anti-tumor effect as compared with a therapy with gemcitabine, paclitaxel or a combination thereof; as well as an anti-tumor effect enhancer.

In view of the above, the present inventors have studied combination use of various drugs, and as a result, have found that combination use of paclitaxel and Compound A exhibits significant anti-tumor effect. The present invention has been completed based on these findings.

That is, the present invention provides the following.

(1) An anti-tumor agent comprising paclitaxel or a salt thereof and 1-(2-deoxy-2-fluoro-4-thio-β-D-arabinofuranosyl)cytosine or a salt or prodrug thereof.

(2) The anti-tumor agent according to (1), in which the amount of the 1-(2-deoxy-2-fluoro-4-thio-β-D-arabinofuranosyl)cytosine or the salt or prodrug thereof used is 0.01 to 100-fold molar amount of the paclitaxel or the salt thereof.

(3) The anti-tumor agent according to (1) or (2), in which the anti-tumor agent is for pancreatic cancer.

(4) The anti-tumor agent according to any one of (1) to (3), in which the paclitaxel is a nanoparticle containing paclitaxel and albumin.

(5) The anti-tumor agent according to any one of (1) to (4), in which the paclitaxel is nab-paclitaxel.

(6) An anti-tumor effect enhancer, comprising 1-(2-deoxy-2-fluoro-4-thio-β-D-arabinofuranosyl)cytosine or a salt or prodrug thereof to be used in combination with paclitaxel or a salt thereof.

(7) An anti-tumor kit comprising a preparation containing paclitaxel or a salt thereof and a preparation containing 1-(2-deoxy-2-fluoro-4-thio-β-D-arabinofuranosyl)cytosine or a salt or prodrug thereof.

(8) An anti-tumor agent comprising 1-(2-deoxy-2-fluoro-4-thio-β-D-arabinofuranosyl)cytosine or a salt or prodrug thereof to be used in combination with paclitaxel or a salt thereof.

(6-1) The anti-tumor effect enhancer according to (6), in which the paclitaxel is a nanoparticle containing paclitaxel and albumin.

(6-2) The anti-tumor effect enhancer according to (6) or (6-1), in which the paclitaxel is nab-paclitaxel.

(7-1) The anti-tumor kit according to (7), in which the paclitaxel is a nanoparticle containing paclitaxel and albumin.

(7-2) The anti-tumor kit according to (7) or (7-1), in which the paclitaxel is nab-paclitaxel.

(8-1) The anti-tumor agent according to (8), in which the paclitaxel is a nanoparticle containing paclitaxel and albumin.

(8-2) The anti-tumor agent according to (8) or (8-1), in which the paclitaxel is nab-paclitaxel.

(9) A method for use of paclitaxel or a salt thereof and 1-(2-deoxy-2-fluoro-4-thio-β-D-arabinofuranosyl)cytosine or a salt or prodrug thereof in the treatment of a tumor, preferably the treatment of pancreatic cancer, comprising a step of administering a therapeutically effective dose thereof to a subject (a mammal including a human) in need of such treatment.

(10) A method for treating a tumor, characterized in that a therapeutically effective dose of 1-(2-deoxy-2-fluoro-4-thio-β-D-arabinofuranosyl)cytosine or a salt or prodrug thereof in the case of being used in combination therapy and a therapeutically effective dose of paclitaxel or a salt thereof in the case of being used in combination therapy are administered in combination to a subject.

(11) A method for treating a tumor, characterized in that a therapeutically effective dose of 1-(2-deoxy-2-fluoro-4-thio-β-D-arabinofuranosyl)cytosine or a salt or prodrug thereof in the case of being used in combination therapy and a therapeutically effective dose of paclitaxel or a salt thereof in the case of being used in combination therapy are administered to a subject simultaneously, separately, sequentially, or at intervals.

(12) Use of 1-(2-deoxy-2-fluoro-4-thio-β-D-arabinofuranosyl)cytosine or a salt or prodrug thereof for the production of an anti-tumor agent in combination with paclitaxel or a salt thereof.

(13) Use of 1-(2-deoxy-2-fluoro-4-thio-β-D-arabinofuranosyl)cytosine or a salt or prodrug thereof for an anti-tumor agent in combination with paclitaxel or a salt thereof.

(14) 1-(2-deoxy-2-fluoro-4-thio-β-D-arabinofuranosyl)cytosine or a salt or prodrug thereof for treating a tumor by administration thereof as a single dosage form with paclitaxel or a salt thereof or as a dosage form separate from paclitaxel or a salt thereof.

Compound A or a salt or prodrug thereof exhibits significant anti-tumor effect in the case of being used in combination with paclitaxel. That is, the anti-tumor agent and anti-tumor kit of the present invention have superior tumor regression and tumor growth inhibitory effects as compared with gemcitabine alone, paclitaxel alone, or a combination of gemcitabine and paclitaxel. The anti-tumor effect enhancer of the present invention can be administered in combination with paclitaxel or a salt thereof to enhance anti-tumor effect.

DESCRIPTION OF THE PREFERRED EMBODIMENTS

Figure 1:
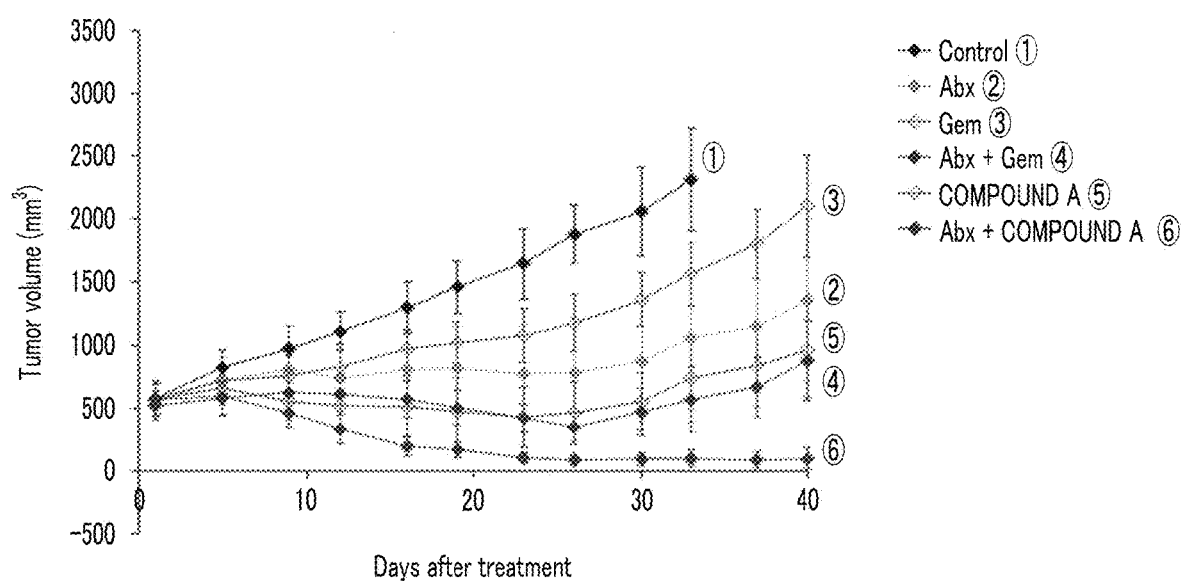
FIG. 1 is a graph showing the transition of tumor volume in a human pancreatic cancer cell line Capan-1 subcutaneously implanted tumor-bearing model mouse.

In the present invention, the numerical value represented by "%" is based on the mass unless otherwise stated. In addition, the range expressed by "to" includes the values at both ends unless otherwise stated.

The term "subject" is a mammal such as a human, a mouse, a monkey, or a livestock in need of prevention or treatment thereof, preferably a human in need of prevention or treatment thereof.

The term "preventing" refers to inhibition of disease onset, reduction of disease onset risk, or delay of disease onset.

The term "treating" refers to improvement of, or inhibition (maintenance or delay) of progression of a target disease or condition.

The term "treatment" refers to preventing, treating, or the like of a variety of diseases.

The term "tumor" refers to a benign tumor or a malignant tumor.

The term "benign tumor" refers to a tumor in which a tumor cell and a sequence thereof take a form close to a normal cell from which such a tumor cell is derived, and which is free of invasiveness or metastatic properties.

The term "malignant tumor" refers to a tumor in which the morphology and sequence of a tumor cell are different from a normal cell from which such a tumor cell is derived, and which exhibits invasiveness or metastatic properties.

Hereinafter, the present invention will be described in detail.

The present invention relates to an anti-tumor agent including paclitaxel or a pharmaceutically acceptable salt thereof (hereinafter, sometimes referred to as a "salt thereof") and 1-(2-deoxy-2-fluoro-4-thio-β-D-arabinofuranosyl)cytosine (Compound A) or a salt or prodrug thereof. Further, the present invention also relates to an anti-tumor agent including paclitaxel or a salt thereof in combination with Compound A or a salt or prodrug thereof.

First, Compound A or a salt or prodrug thereof will be described.

The salt may be, for example, a pharmaceutically acceptable salt and specific examples thereof include a mineral acid salt, an organic carboxylate, and a sulfonate. Preferred examples of the salt include a mineral acid salt and a sulfonate.

Examples of the mineral acid salt include hydrochloride, hydrobromide, hydroiodide, nitrate, phosphate, and sulfate, among which hydrochloride, hydroiodide, nitrate, or sulfate is preferable, and hydrochloride is more preferable. Examples of the organic carboxylate include formate, acetate, citrate, oxalate, fumarate, maleate, succinate, malate, tartrate, aspartate, trichloroacetate, and trifluoroacetate. Examples of the sulfonate include methanesulfonate, benzenesulfonate, p-toluenesulfonate, mesitylenesulfonate, and naphthalenesulfonate, among which methanesulfonate is preferable.

The salt of Compound A may be an anhydride, a hydrate, or a solvate. In the case where the term "salt" is simply used in the present specification, it may be in the form of anhydride, hydrate, or solvate. As for the term "anhydride" used in the present specification, it refers to the salt in a state where it is not a hydrate or a solvate, unless otherwise stated. Even though it is a substance which originally does not form a hydrate or a solvate, the salt of Compound A which does not have crystallization water, hydration water and an interacting solvent is also included in the "anhydride" referred to in the present invention. Anhydride may also be referred to as "anhydrate". In the case where the salt of Compound A is a hydrate, the molecular number of hydration water is not particularly limited, and the hydrate may be a monohydrate, a dihydrate, or the like. Examples of the solvate include methanol solvate, ethanol solvate, propanol solvate, and 2-propanol solvate.

Particularly preferred specific examples of Compound A are as follows:

methanesulfonate of 1-(2-deoxy-2-fluoro-4-thio-β-D-arabinofuranosyl)cytosine;

hydrochloride of 1-(2-deoxy-2-fluoro-4-thio-β-D-arabinofuranosyl)cytosine;

½ sulfate of 1-(2-deoxy-2-fluoro-4-thio-β-D-arabinofuranosyl)cytosine;

nitrate of 1-(2-deoxy-2-fluoro-4-thio-β-D-arabinofuranosyl)cytosine; and hydroiodide of 1-(2-deoxy-2-fluoro-4-thio-β-D-arabinofuranosyl)cytosine; as well as anhydrides of the foregoing salts.

The prodrug refers to a compound or a salt thereof which is converted into a compound exhibiting a desired pharmacological activity, following cleavage of a functional group functioning as a prodrug by a reaction with an enzyme, gastric juice, or the like in the body after administration thereof.

Examples of groups forming a prodrug include the groups described in Stella V J et al., Prodrugs: Challenges and Rewards. Parts 1 and 2, 2007, American Association of Pharmaceutical Scientists.

The prodrug of Compound A refers to a compound or a salt thereof which converts into Compound A or a phosphate compound thereof by a reaction with an enzyme, gastric juice, or the like under physiological conditions in vivo.

As to the prodrug of Compound A, the description of WO2016/068341A, the contents of which are incorporated herein, can be incorporated and referred to.

More specifically, for example, a thionucleoside derivative represented by General Formula [1] or a salt thereof described in WO2016/068341A is incorporated herein, and a preferred range thereof is also the same as that described in WO2016/068341A.

In the present invention, Compound A or a salt or prodrug thereof may be used alone or in combination of two or more thereof.

Next, a method for producing Compound A or a salt or prodrug thereof will be described. Compound A can be produced, for example, by the method described in WO1997/038001A or Journal of Organic Chemistry, 1999, Vol. 64, pp. 7912 to 7920. The salt of Compound A or a hydrate or solvate thereof can be produced, for example, by the method described in WO2014/027658A. The prodrug of Compound A can be produced, for example, by the method described in WO2016/068341A.

Compound A or a salt or prodrug thereof according to the present invention can be used as an anti-tumor agent or as an active ingredient of a pharmaceutical composition.

In the present invention, paclitaxel or a salt thereof may be used alone or in combination of two or more thereof. Paclitaxel or a salt thereof may be a composition containing them, in addition to paclitaxel or a salt thereof.

The salt may be, for example, a pharmaceutically acceptable salt and specific examples thereof include salts in commonly known basic groups such as amino group, and salts in commonly known acidic groups such as hydroxyl group and carboxyl group.

Examples of salts in basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Examples of salts in acidic groups include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Examples of the composition containing paclitaxel or a salt thereof include a nanoparticle containing paclitaxel and albumin (preferably human serum albumin) (albumin-bound paclitaxel injection suspension of nanoparticle preparation encapsulating paclitaxel with albumin (nab-paclitaxel, trade name "Abraxane")); a polymeric micelle (NK 105) in which paclitaxel is encapsulated in a block copolymer of polyethylene glycol and polyaspartic acid; a prodrug in which fatty acid docosahexaenoic acid (DHA) is conjugated to paclitaxel (Taxoprexin); a prodrug in which polyglutamic acid is conjugated to paclitaxel (trade name "Opaxio"); and a prodrug in which a monoclonal antibody targeting a tumor cell is conjugated to paclitaxel.

Paclitaxel is preferably a nanoparticle containing paclitaxel and albumin and more preferably nab-paclitaxel.

Compound A is an anti-tumor agent having an excellent DNA synthesis inhibitory effect. In the case where Compound A is used in combination with paclitaxel, it is expected that such a combination will have an effect of enhancing the anti-tumor effect of paclitaxel without showing significant exacerbation of toxicity.

(Anti-Tumor Agent)

According to the present invention, provided are an anti-tumor agent including paclitaxel or a salt thereof and 1-(2-deoxy-2-fluoro-4-thio-β-D-arabinofuranosyl)cytosine or a salt or prodrug thereof; and an anti-tumor agent including 1-(2-deoxy-2-fluoro-4-thio-β-D-arabinofuranosyl)cytosine or a salt or prodrug thereof to be used in combination with paclitaxel or a salt thereof.

Typically, the anti-tumor agent of the embodiment of the present invention may contain additives such as an excipient, a binder, a lubricant, a disintegrant, a coloring agent, a flavoring agent, an emulsifier, a surfactant, a solubilizing agent, a suspending agent, a tonicity agent, a buffering agent, a preservative, an antioxidant, a stabilizer, and an absorption promoter, which have been used in the formulation.

The anti-tumor agent of the embodiment of the present invention including paclitaxel or a salt thereof and Compound A or a salt or prodrug thereof may be a single dosage form containing paclitaxel or a salt thereof and Compound A or a salt or prodrug thereof, or may be a binary dosage form containing paclitaxel or a salt thereof and Compound A or a salt or prodrug thereof. Preferably, the anti-tumor agent of the embodiment of the present invention is a binary dosage form in which paclitaxel or a salt thereof and Compound A or a salt or prodrug thereof are separately formulated.

In the case where paclitaxel or a salt thereof and Compound A or a salt or prodrug thereof are used as separate preparations, individual preparations can be administered to a subject simultaneously, separately, sequentially, or at intervals. In addition, the means for administering a composition containing paclitaxel and the means for administering a composition containing Compound A may be the same or different (for example, oral administration and injection).

The route of administration of the anti-tumor agent of the embodiment of the present invention may be, for example, a method such as intravenous, intraarterial, rectal, intraperitoneal, intramuscular, intratumoral or intravesical injection, oral administration, transdermal administration and/or through suppositories.

Parenteral administration is preferred as the route of administration. For example, intravenous injection (intravenous infusion) such as drip infusion, intramuscular injection, intraperitoneal injection, subcutaneous injection, intraocular injection and/or intrathecal injection can be mentioned as the parenteral administration. The method of administration includes administration by syringe or drip infusion.

The dose or blending amount of paclitaxel or a salt thereof and Compound A or a salt or prodrug thereof contained in the anti-tumor agent of the embodiment of the present invention is not particularly limited as long as it exerts an effect of enhancing the anti-tumor effect, but Compound A or a salt or prodrug thereof may be used in an amount of 0.01 to 100 mol, preferably 0.1 to 50 mol, and more preferably 1 to 40 mol per 1 mol of paclitaxel.

With respect to the dosage and administration frequency of paclitaxel or a salt thereof, for example, for an adult, for example a dose of 1 to 1000 mg/m$^2$/day can be administered once or in several divided portions by oral or parenteral administration (for example, injection, drip infusion, or rectal administration).

With respect to the dosage and administration frequency of Compound A or a salt or prodrug thereof, a dose of 1 to 2000 mg/m$^2$/day can be administered once or in several divided portions. However, it is not limited to these doses and administration frequencies.

Examples of dosage forms of the anti-tumor agent of the embodiment of the present invention include a tablet, a capsule, a powder, a syrup, a granule, a pill, a suspension, an emulsion, a solution, a suppository, an eye drop, a nasal drop, an ear drop, a patch, an ointment, and an injection, among which an injection is preferred. Each of these dosage forms can be produced by a formulation method conventionally known to those skilled in the art.

The anti-tumor agent of the embodiment of the present invention can be effectively used for the treatment of various types of tumors including, for example, melanoma, liver cancer, glioma, neuroblastoma, sarcoma, and tumors of the lung, colon, breast, bladder, ovary, testis, prostate, cervix, pancreas, stomach, small intestine and other organs. The anti-tumor agent of the embodiment of the present invention is preferably an antineoplastic agent, can be used as an anticancer agent, and is particularly effective for the treatment of pancreatic cancer.

(Anti-Tumor Kit)

The anti-tumor kit of the embodiment of the present invention is a kit including a combination of (a) paclitaxel or a salt thereof and (b) Compound A or a salt or prodrug thereof.

In the kit, (a) paclitaxel or a salt thereof and (b) Compound A or a salt or prodrug thereof can each be in various known preparation forms, and depending on the preparation form, (a) and (b) are contained in various commonly used containers.

Further, in the kit, (a) paclitaxel or a salt thereof and (b) Compound A or a salt or prodrug thereof may be contained in separate containers or may be mixed and stored in the same container. It is preferred that (a) paclitaxel or a salt thereof and (b) Compound A or a salt or prodrug thereof are contained in separate containers.

(Anti-Tumor Effect Enhancer)

The anti-tumor effect enhancer of the embodiment of the present invention is an anti-tumor agent including 1-(2-deoxy-2-fluoro-4-thio-β-D-arabinofuranosyl)cytosine or a salt or prodrug thereof to be used in combination with paclitaxel or a salt thereof.

Typically, the anti-tumor effect enhancer of the embodiment of the present invention may contain additives such as an excipient, a binder, a lubricant, a disintegrant, a coloring agent, a flavoring agent, an emulsifier, a surfactant, a solubilizing agent, a suspending agent, a tonicity agent, a buffering agent, a preservative, an antioxidant, a stabilizer, and an absorption promoter, which have been used in the formulation.

The anti-tumor effect enhancer of the embodiment of the present invention can be administered to a subject simultaneously with, separately from, sequentially with, or at intervals with paclitaxel or a salt thereof.

Parenteral administration is preferred as the route of administration of the anti-tumor effect enhancer of the embodiment of the present invention. For example, intravenous injection (intravenous infusion) such as drip infusion, intramuscular injection, intraperitoneal injection, subcutaneous injection, intraocular injection and/or intrathecal injection can be mentioned as the parenteral administration. The method of administration includes administration by syringe or drip infusion.

The dose or blending amount of Compound A or a salt or prodrug thereof contained in the anti-tumor effect enhancer of the embodiment of the present invention is not particularly limited as long as it exerts an effect of enhancing the anti-tumor effect, but Compound A or a salt or prodrug thereof may be used in an amount of 0.01 to 100 mol, preferably 0.1 to 50 mol, and more preferably 1 to 40 mol per 1 mol of paclitaxel.

With respect to the dosage and administration frequency of Compound A or a salt or prodrug thereof contained in the anti-tumor effect enhancer of the embodiment of the present invention, a dose of 1 to 2000 mg/m$^2$/day can be administered once or in several divided portions. However, it is not limited to these doses and administration frequencies.

The anti-tumor effect enhancer of the embodiment of the present invention can be effectively used for the treatment of various types of tumors including, for example, melanoma, liver cancer, glioma, neuroblastoma, sarcoma, and tumors of the lung, colon, breast, bladder, ovary, testis, prostate, cervix, pancreas, stomach, small intestine and other organs. The anti-tumor effect enhancer of the embodiment of the present invention is preferably an antineoplastic effect enhancer, and is particularly effective for the treatment of pancreatic cancer.

The present invention provides a method for use of paclitaxel or a salt thereof and 1-(2-deoxy-2-fluoro-4-thio-β-D-arabinofuranosyl)cytosine or a salt or prodrug thereof in the treatment of a tumor, preferably the treatment of pancreatic cancer, including a step of administering a therapeutically effective dose thereof to a subject (a mammal including a human) in need of such treatment.

Further, the present invention provides a method for treating a tumor, characterized in that a therapeutically effective dose of 1-(2-deoxy-2-fluoro-4-thio-β-D-arabinofuranosyl)cytosine or a salt or prodrug thereof in the case of being used in combination therapy and a therapeutically effective dose of paclitaxel or a salt thereof in the case of being used in combination therapy are administered in combination to a subject.

Further, the present invention provides a method for treating a tumor, characterized in that a therapeutically effective dose of 1-(2-deoxy-2-fluoro-4-thio-β-D-arabinofuranosyl)cytosine or a salt or prodrug thereof in the case of being used in combination therapy and a therapeutically effective dose of paclitaxel or a salt thereof in the case of being used in combination therapy are administered to a subject simultaneously, separately, sequentially, or at intervals.

Use of 1-(2-deoxy-2-fluoro-4-thio-β-D-arabinofuranosyl)cytosine or a salt or prodrug thereof can be made for the production of an anti-tumor agent in combination with paclitaxel or a salt thereof.

Use of 1-(2-deoxy-2-fluoro-4-thio-β-D-arabinofuranosyl)cytosine or a salt or prodrug thereof can be made for an anti-tumor agent in combination with paclitaxel or a salt thereof.

According to the present invention, it is possible to obtain 1-(2-deoxy-2-fluoro-4-thio-β-D-arabinofuranosyl)cytosine or a salt or prodrug thereof for treating a tumor by administration thereof as a single dosage form with paclitaxel or a salt thereof or as a dosage form separate from paclitaxel or a salt thereof.

Further, according to the present invention, it is possible to obtain an anti-tumor agent including 1-(2-deoxy-2-fluoro-4-thio-β-D-arabinofuranosyl)cytosine or a salt or prodrug thereof, which is used in combination with paclitaxel or a salt thereof.

EXAMPLES

Hereinafter, the present invention will be described in more detail with reference to Examples and Test Examples, but the present invention is not limited to these Examples and the like. In addition, the maximum tolerated dose (MTD) indicated by paper reports and the like was used for setting doses of various anti-tumor agents whose anti-tumor effect is enhanced as shown in the following Test Examples.

Example 1

Methanesulfonate of 1-(2-deoxy-2-fluoro-4-thio-β-D-arabinofuranosyl)cytosine (Compound A) was synthesized by the method described in WO2013/146833A.

Test Example 1

Combinational effect test in Capan-1 subcutaneously implanted tumor-bearing model mouse Gemcitabine (hereinafter, also referred to as Gem), Abraxane (hereinafter, also referred to as Abx), and methanesulfonate of Compound A were used as test substances.

Gemcitabine was prepared by dissolving gemcitabine hydrochloride (manufactured by Teva Pharmaceutical Industries Limited) in physiological saline. Abraxane was prepared by dissolving Abraxane (manufactured by Celgene Corporation) in physiological saline.

Capan-1 cell, a human pancreatic cancer cell line, was subcutaneously injected into the posterior flank of 5 to 6-week old female BALB/cA Jcl-nu mice. After tumor implantation, the major diameter (mm) and minor diameter (mm) of the tumor were measured, and the tumor volume (TV) was calculated. Mice were assigned to each group so that the average TV of each group was equal, and the day on which this grouping (n=8) was carried out was taken as Day 1.

The test liquid in Abraxane alone group was prepared to be 30 mg/kg/day as the administration dose. In addition, the test liquid in Compound A alone group was prepared to be 480 mg/kg/day. Compound A was administered from the mouse tail vein a total of three times from Day 1 once a week, and Abraxane was similarly administered from the mouse tail vein a total of three times from Day 1 once a week. In the combined administration group, Compound A was administered at 480 mg/kg/day and Abraxane was administered at 30 mg/kg/day.

As a comparative experiment, gemcitabine was used as a control. The test liquid of gemcitabine alone group was prepared to be 240 mg/kg/day. Gemcitabine was administered from the mouse tail vein a total of three times from Day 1 once a week. In the combined administration group, gemcitabine was administered at 240 mg/kg/day and Abraxane was administered at 30 mg/kg/day.

In this test, doses of Compound A and gemcitabine were set using MTD of each drug. Abraxane was used at the maximum dose usable in combination with each drug. An anti-tumor agent exhibits that the dose exhibiting the maximum drug efficacy is very close to the dose expressing toxicity, and the anti-tumor agent is generally evaluated in the vicinity of MTD in order to evaluate the maximum anti-tumor effect possessed by the drug in an animal model. In this test example, the MTD and the maximum effect dose are almost synonymous.

As an index of anti-tumor effect, TV at Day 33 was measured in each drug administration group. According to the following equation, a relative tumor volume (RTV) with respect to Day 1 and T/C (%) were calculated to evaluate the anti-tumor effect. Evaluation judgment of combinational effect was made as having a combinational effect in the case where the average RTV value of the combined administration group was statistically significantly (Welch's IUT, over all maximum p<0.05) smaller than the average RTV value of each individual administration group. The results are shown in Table 1 and FIG. 1. In the table, * indicates that a statistically significant difference was observed in the control group and Gem or Compound A alone group.

TV (mm$^3$)=(major diameter×minor diameter$^2$)/2

RTV=(TV at Day 33)/(TV at Day 1)

T/C (%)=[(average RTV value of test liquid administered group)/(average RTV value of control group)]×100

TABLE 1

| Group name | Dose (mg/kg/day) | RTV (mean ± standard deviation) | T/C (%) | vs. control | vs. alone |
|---|---|---|---|---|---|
| Control | 0 | 4.01 ± 0.21 | 100 | — | — |
| Abx | 30 | 2.03 ± 1.11 | 50.6 | * | — |
| Gem | 240 | 2.74 ± 0.41 | 68.3 | * | — |
| Abx + Gem | 30 + 240 | 1.11 ± 0.48 | 27.7 | * | * |
| Compound A | 480 | 1.29 ± 0.59 | 32.2 | * | — |
| Abx + Compound A | 30 + 480 | 0.21 ± 0.12 | 5.2 | * | * |

* statistically significant

Compound A significantly enhanced the anti-tumor effect of Abraxane. At 480 mg/kg/day, which is a high dose (maximum effect dose) in nude mice, combination use thereof induced significant reduction in the size of the tumor. The effect was thought to be larger than that of the existing drug gemcitabine. A more detailed explanation will be given later.

Figure 2:
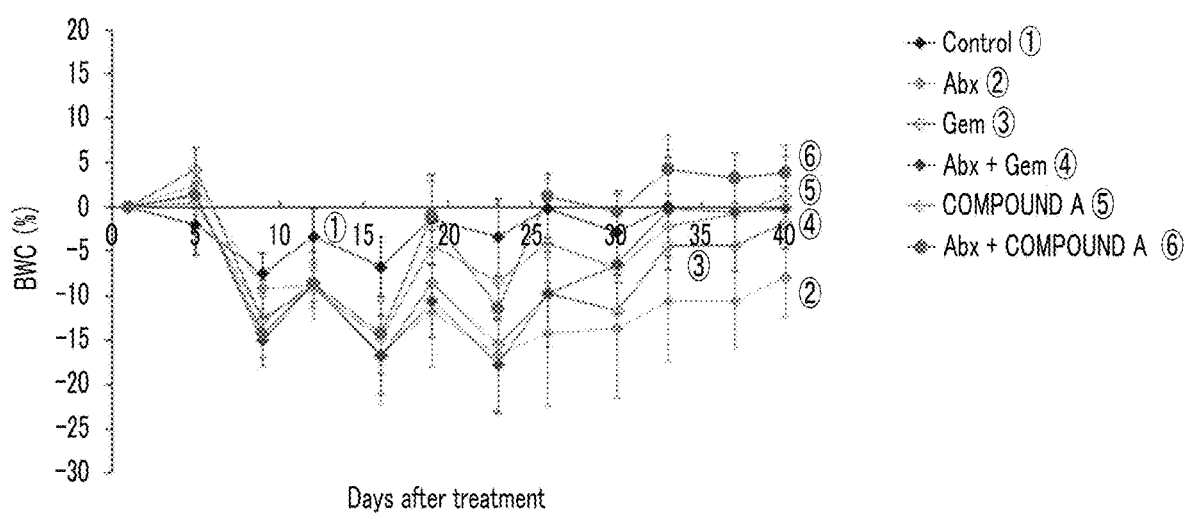
FIG. 2 is a graph showing the transition of body weight in a human pancreatic cancer cell line Capan-1 subcutaneously implanted tumor-bearing model mouse.

Also, body weight (BW) was measured over time as an index of toxicity and an average % body weight change (BWC (%)) up to Day 33 relative to Day 1 was calculated by the following equation (n: weight measurement day, last measurement day corresponds to Day 33 which is the final evaluation day). The results are shown in FIG. 2.

BWC (%)=[(BW at Day $n$)−(BW at Day 1)]/(BW at Day 1)×100

No exacerbation of body weight loss was observed in combined administration.

On the combinational effect of the present invention, the results of evaluation using a combination index (CI) which is a quantitative index of the combinational effect are shown. The CI can be calculated by the following equation according to Cancer Research, 2010, Vol. 70, pp. 440 to 446.

That is, in the case where the drugs to be used in combination are drugs 1 and 2, CI=(T/C at the time of combination use)÷100/{[(T/C of drug 1)÷100]×[(T/C of drug 2)÷100]}

CI=1: additive effect

CI>1: antagonistic effect

CI<1: synergistic effect

The CI in the case where Abraxane and gemcitabine were used in combination was 0.80, and the CI in the case where Abraxane and Compound A were used in combination was 0.32. Since CI<1, a synergistic effect by combination use is observed, and the synergistic effect of Compound A can be said to be more significant than that of the existing drug gemcitabine.

In addition, on the combinational effect of the present invention, the results of evaluation using a tumor growth inhibitory effect (growth of control (GC)) are shown. For the evaluation method, the same method as in B of FIG. 5 of Molecular Cancer Therapeutics, 2013, Vol. 12, pp. 2585 to 2696 was used.

As described in the above document, the GC can be calculated by the following equation.

In the case where RTV>1 GC (%)=[(corresponding drug RTV-1)/(control RTV-1)]×100   [1]

In the case where RTV≤1 GC (%)=(corresponding drug RTV-1)×100   [2]

Figure 3:
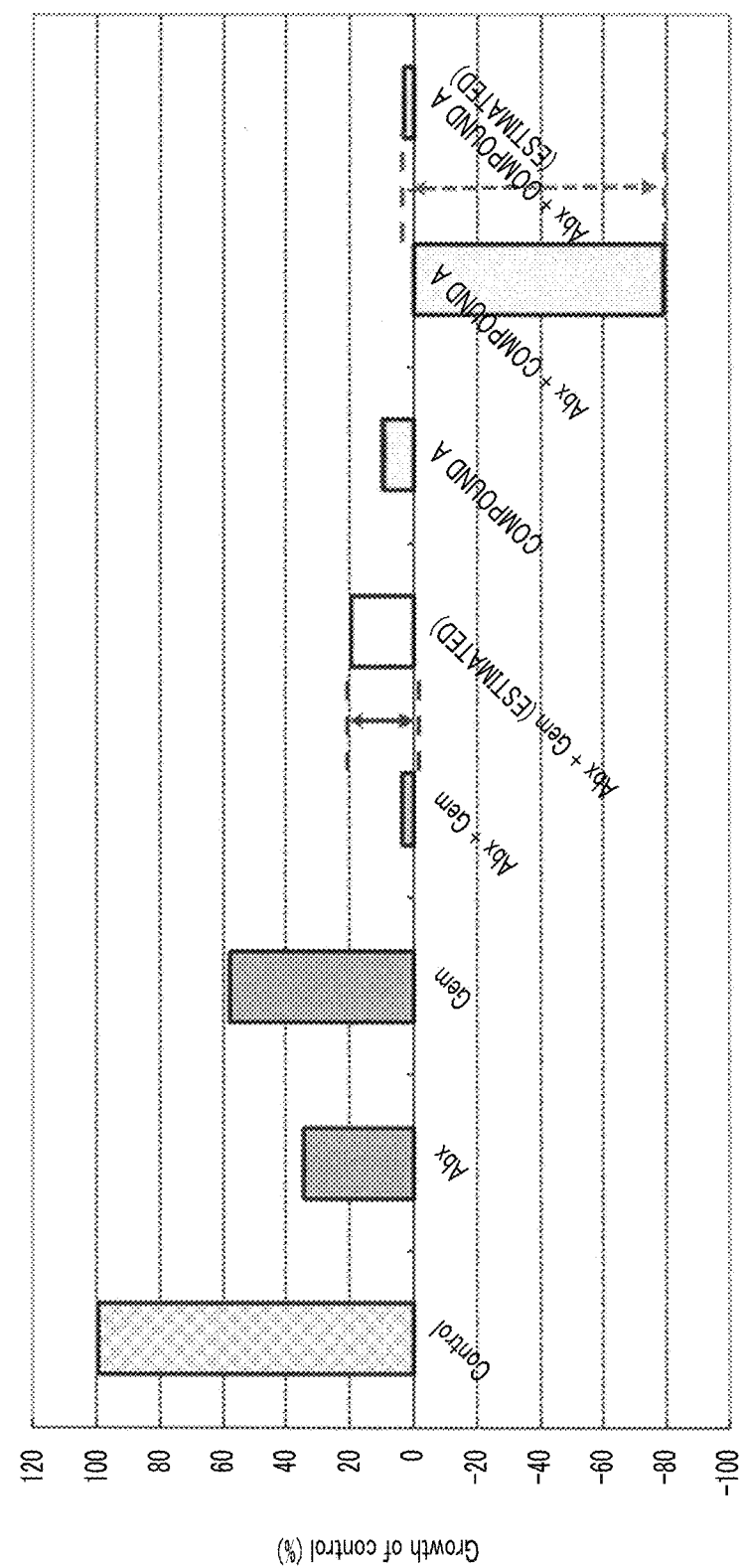
FIG. 3 is a graph showing a combinational effect of inhibiting tumor growth in a human pancreatic cancer cell line Capan-1 subcutaneously implanted tumor-bearing model mouse.

Combinational effect was estimated from the drug efficacy with Abraxane and Compound A or gemcitabine alone by the following calculation equation. The results are shown in FIG. 3 and Table 2.

The estimated combination use GC (%)=[GC (%) of Abraxane×drug alone GC (%)]÷100

For example, in this test example, from Table 1, GC (%) of Abraxane alone is

[(2.03−1)/(4.01−1)]×100=34.2 (%) since RTV>1,

GC (%) of gemcitabine is [(2.74−1)/(4.01−1)]×100=57.8 (%) since RTV>1.

Therefore, the estimated combination use GC (%) is (34.2×57.8)÷100=19.8 (%).

On the other hand, the actual GC (%) of the combination use of Abraxane and gemcitabine is [(1.11−1)/(4.01−1)]×100=3.7 (%) from RTV>1.

As a result, since the estimated combination use GC (%) is 19.8 (%), whereas the actual combination use GC (%) is 3.7 (%), it is thought that there is a significant combinational effect exceeding the assumed combinational effect.

In the case where the same calculation is carried out also for Compound A, GC (%) of Compound A is [(1.29−1)/(4.01−1)]×100=9.6 (%) since RTV>1 for single drug.

Therefore, the estimated combination use GC (%) is (34.2×9.6)÷100=3.3 (%)

The actual GC (%) is (0.21−1)×100=−79.0 (%) from RTV≤1. The solid arrow in FIG. 3 indicates the combinational effect of gemcitabine and the dotted arrow indicates the combinational effect of Compound A.

As a result, also in Compound A, the estimated combination use GC (%) is 3.3 (%), whereas the actual combination use GC (%) is −79.0 (%), from which it is thought that there is a significant combinational effect exceeding the assumed combinational effect. It can be said that the degree of combinational effect is more prominent than the existing drug gemcitabine.

TABLE 2

| | Dose (mg/kg/day) | RTV (mean ± standard deviation) | GC (%) | Estimated combination use GC (%) |
|---|---|---|---|---|
| Control | 0 | 4.01 ± 0.21 | — | — |
| Abx | 30 | 2.03 ± 1.11 | 34.2 | — |
| Gem | 240 | 2.74 ± 0.41 | 57.8 | — |
| Abx + Gem | 30 + 240 | 1.11 ± 0.48 | 3.7 | 19.8 |
| Compound A | 480 | 1.29 ± 0.59 | 9.6 | — |
| Abx + Compound A | 30 + 480 | 0.21 ± 0.12 | −79.0 | 3.3 |

The present invention is useful as an anti-tumor agent and an anti-tumor kit which exhibit significant anti-tumor effect, as well as an anti-tumor effect enhancer.

What is claimed is:

1. A method for use of paclitaxel or a salt thereof and 1-(2-deoxy-2-fluoro-4-thio-β-D-arabinofuranosyl)cytosine or a salt or prodrug thereof in the treatment of a tumor in a mammal, comprising administering a therapeutically effective dose of paclitaxel or a salt thereof and a therapeutically effective dose of 1-(2-deoxy-2-fluoro-4-thio-β-D-arabinofuranosyl)cytosine or a salt or prodrug thereof to a mammal in need of such treatment,
   wherein the tumor is pancreatic cancer,
   the paclitaxel is nab-paclitaxel, and
   the amount of the 1-(2-deoxy-2-fluoro-4-thio-β-D-arabinofuranosyl)cytosine or the salt or prodrug thereof used is 1 to 100-fold molar amount of the paclitaxel or the salt thereof.

2. The method according to claim 1, wherein the paclitaxel is a nanoparticle containing paclitaxel and albumin.

3. The method according to claim 1, wherein the amount of the 1-(2-deoxy-2-fluoro-4-thio-β-D-arabinofuranosyl)cytosine or the salt or prodrug thereof used is 1 to 52-fold molar amount of the paclitaxel or the salt thereof.

4. A method for treating a tumor in a mammal, comprising administering a therapeutically effective dose of 1-(2-deoxy-2-fluoro-4-thio-β-D-arabinofuranosyl)cytosine or a salt or prodrug thereof and a therapeutically effective dose of paclitaxel or a salt thereof in combination to a mammal, each of said therapeutically effective doses meaning a therapeutically effective dose used in combination therapy,
   wherein the tumor is pancreatic cancer,
   the paclitaxel is nab-paclitaxel, and
   the amount of the 1-(2-deoxy-2-fluoro-4-thio-β-D-arabinofuranosyl)cytosine or the salt or prodrug thereof used is 1 to 100-fold molar amount of the paclitaxel or the salt thereof.

5. The method according to claim 4, wherein the paclitaxel is a nanoparticle containing paclitaxel and albumin.

6. The method according to claim 4, wherein the amount of the 1-(2-deoxy-2-fluoro-4-thiod-β-D-arabinofuranosyl)cytosine or the salt or prodrug thereof used is 1 to 52-fold molar amount of the paclitaxel or the salt thereof.

7. A method for treating a tumor in a mammal comprising administering a therapeutically effective dose of 1-(2-deoxy-2-fluoro-4-thio-β-D-arabinofuranosyl)cytosine or a salt or prodrug thereof and a therapeutically effective dose of paclitaxel or a salt thereof to a mammal simultaneously, separately, sequentially, or at intervals, each of said therapeutically effective doses meaning a therapeutically effective dose used in combination therapy, wherein the tumor is pancreatic cancer, the paclitaxel is nab-paclitaxel, and the amount of the 1-(2-deoxy-2-fluoro-4-thio-β-D-arabinofuranosyl)cytosine or the salt or prodrug thereof used is 1 to 100-fold molar amount of the paclitaxel or the salt thereof.

8. The method according to claim 7, wherein the paclitaxel is a nanoparticle containing paclitaxel and albumin.

9. The method according to claim 7, wherein the amount of the 1-(2-deoxy-2-fluoro-4-thio-β-D-arabinofuranosyl)cytosine or the salt or prodrug thereof used is 1 to 52-fold molar amount of the paclitaxel or the salt thereof.

10. A method for enhancing an anti-tumor effect in a mammal comprising administering a 1-(2-deoxy-2-fluoro-4-thio-β-D-arabinofuranosyl)cytosine or a salt or prodrug thereof in combination with paclitaxel or a salt thereof, to a mammal, wherein the tumor is pancreatic cancer, the paclitaxel is nab-paclitaxel, and the amount of the 1-(2-deoxy-2-fluoro-4-thio-β-D-arabinofuranosyl)cytosine or the salt or prodrug thereof used is 1 to 100-fold molar amount of the paclitaxel or the salt thereof.

11. The method according to claim 10, wherein the paclitaxel is a nanoparticle containing paclitaxel and albumin.

12. The method according to claim 10, wherein the amount of the 1-(2-deoxy-2-fluoro-4-thio-β-D-arabinofuranosyl)cytosine or the salt or prodrug thereof used is 1 to 52-fold molar amount of the paclitaxel or the salt thereof.

* * * * *

UNITED STATES PATENT AND TRADEMARK OFFICE
CERTIFICATE OF CORRECTION

| | | |
|---|---|---|
| PATENT NO. | : 11,369,625 B2 | Page 1 of 1 |
| APPLICATION NO. | : 16/286930 | |
| DATED | : June 28, 2022 | |
| INVENTOR(S) | : Yoshihide Iwaki, Tsukasa Kitahashi and Shinji Mima | |

It is certified that error appears in the above-identified patent and that said Letters Patent is hereby corrected as shown below:

On the Title Page

Please insert:
-- (30) Foreign Application Priority Data
August 31, 2016 (JP) 2016-169167 --

Signed and Sealed this
Thirty-first Day of January, 2023

*Katherine Kelly Vidal*

Katherine Kelly Vidal
*Director of the United States Patent and Trademark Office*